United States Patent [19]
Tsuboi et al.

[11] Patent Number: 6,063,393
[45] Date of Patent: *May 16, 2000

[54] PLANT TREATMENT AGENTS

[75] Inventors: Shin-ichi Tsuboi, Tochigi; Atsumi Kamochi, Kochi; Nobuhiro Yamashita, Kochi; Ikuya Saito, Kochi; Yuzuru Wada, Hachioji; Kunihiro Isono, Tochigi; Shigeharu Koyama, Oyama, all of Japan

[73] Assignee: Nihon Bayer Agrochem K.K., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/041,077

[22] Filed: Apr. 1, 1993

[30] Foreign Application Priority Data

Apr. 9, 1992 [JP] Japan ................................ 4-115283

[51] Int. Cl.$^7$ ..................................... A01N 25/08
[52] U.S. Cl. ........................ 424/409; 424/405; 424/406; 424/407; 424/408
[58] Field of Search ................................ 424/407, 408, 424/409, 405, 406

[56] References Cited

U.S. PATENT DOCUMENTS

| | | |
|---|---|---|
| 1,661,577 | 3/1928 | Renner et al. . |
| 3,068,087 | 12/1962 | Davis . |
| 4,291,497 | 9/1981 | Manankov . |
| 4,401,454 | 8/1983 | Fritz et al. .............................. 504/165 |
| 4,666,706 | 5/1987 | Farquharoon et al. ................. 424/408 |
| 4,743,448 | 5/1988 | Bahadir et al. ......................... 424/405 |
| 5,034,524 | 7/1991 | Shrokawa et al. ...................... 544/124 |
| 5,157,207 | 10/1992 | Carlson et al. ......................... 800/200 |
| 5,201,925 | 4/1993 | Itzel et al. . |

FOREIGN PATENT DOCUMENTS

| | | |
|---|---|---|
| 0179588 | 4/1986 | European Pat. Off. . |
| 0 254 196 | 1/1988 | European Pat. Off. . |
| 2 449 664 | 9/1980 | France . |

*Primary Examiner*—Neil S. Levy
*Attorney, Agent, or Firm*—Norris, McLaughlin & Marcus, P.A.

[57] ABSTRACT

The present invention relates to a process for the treatment of individual plants with solid shaped plant treatment agents which are introduced into the sap conduction paths of the plants, new solid shaped plant treatment agents and their production.

6 Claims, No Drawings

PLANT TREATMENT AGENTS

The present invention relates to a process for the treatment of individual plants with solid shaped plant treatment agents which are introduced into the sap conduction paths of the plants, new solid shaped plant treatment agents and their production.

It has already become known to inject solutions of certain insecticides or to implant pulverulent formulations into the trunks of deciduous and coniferous trees (Chemical Abstracts CA 108: 181 188w; CA 99: 83 692v; CA 99: 181 184; and CA 87: 146 712).

The method is limited to readily water-soluble active compounds having a systemic action. Handling of the method under conditions in practise, that is to say administering an adequate amount of active compound into the sap stream and thereby damaging the plant only minimally not only under experimental purposes on a very few plants, is unsatisfactory.

It has already become known to embed active compounds in a polymer matrix, from which they are released again only slowly. Such slow-release shaped articles are used to release active compounds in the soil over a relatively long time (Chemical Abstract CA 100: 47 099 n; and U.S. Pat. No. 3,269,900). Other polymer/active compound formulations are employed to release readily vapourisable active compounds uniformly into the atmosphere over a relatively long period of time (U.S. Pat. No. 3,318,764). Yet other polymer/active compound formulations are employed to protect animals from parasites. For this, the active compound, which migrates to the polymer surface, is rubbed off mechanically by the coat of the animal and distributed over the animal (U.S. Pat. No. 3,852,416).

In the customary treatment of plants by atomising, spraying, dusting and the like, the active compound is distributed in a suitable formulation as far as possible over the entire surface of the plants. It then either encounters directly the plant pests to be combated, or it has to penetrate the protective layers of the plants in order to arrive at the sites of action via the sap stream of the plant. These treatment methods are associated with a high loss of active compound. The same applies to methods where active compound formulations are used in the root region, in which the active compound is taken up via the roots and arrives at the site of action via the sap stream. Here also, the active compound must be present in the soil in a sufficiently high concentration for the plants to be able to absorb enough active compound.

To match the amount of active compound to be applied as precisely as possible to the actual requirement of the plant, it would be desirable for the required amount of active compound to be introduced directly into the sap stream of the plant. A prerequisite here is, however, that the plant (for example valuable productive fruit trees) is not damaged even after several applications.

The present invention relates to:
1. a process for the treatment of individual plants with solid shaped plant treatment agents in which the active compounds are contained in a matrix of a solid carrier material and which are introduced into the region of the sap conduction paths of the plants.
2. Solid shaped plant treatment agents in which the active compounds are contained in a matrix of a solid carrier material and which are introduced into the region of the sap conduction paths of individual plants.
3. A process for the production of solid shaped plant treatment agents which are introduced into the region of the sap conduction paths of individual plants, characterised in that active compounds are mixed and physically or chemically shaped with substances forming the matrix of a solid carrier.

The process according to the invention is suitable for the treatment of valuable individual plants. These include stock and ornamental plants. Stock and ornamental plants which may be mentioned are: herbaceous plants, annual and perennial shrubs and woody plants, such as bushes and trees.

The herbaceous plants include vegetables, such as tomatoes, paprika, aubergines, cucumbers, melons, cabbage species, potatoes and tobacco. The perennial shrubs include tea and coffee. The woody plants include the known berry- and fruit-bearing woody plants, pomaceous/stone fruit, berries, bananas, citrous, grapevines, palms (for example oil trees), cacao, olives, hops, roses and rhododendron, and also the woody plants used in forestry, such as beech, oak, spruce and fir.

Cuttings, slips, tubers, bulbs and parts of leaf used for propagation may furthermore be mentioned.

Pests which may be mentioned are phytopathogenic insects, arachnids and nematodes, and also fungi and bacteria.

The insects include:
From the order of the Isopoda, for example, *Oniscus asellus, Armadillidium vulgare* and *Porcellio scaber.*
From the order of the Diplopoda, for example, *Blaniulus guttulatus.*
From the order of the Chilopoda, for example, *Geophilus carpophagus* and Scutigera spec.
From the order of the Symphyla, for example, *Scutigerella immaculata.*
From the order of the Thysanura, for example, *Lepisma saccharina.*
From the order of the Collembola, for example, *Onychiurus armatus.*
From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*
From the order of the Dermaptera, for example, *Forficula auricularia.*
From the order of the Isoptera, for example, Reticulitermes spp.
From the order of the Anoplura, for example, *Phylloxera vastatrix,* Pemphigus spp., *Pediculus humanus corporis,* Haematopinus spp. and Linognathus spp.
From the order of the Mallophaga, for example, Trichodectes spp. and Damalinea spp.
From the order of the Thysanoptera, for example, *Hercinothrips femoralis* and *Thrips tabaci.*
From the order of the Heteroptera, for example, Eurygaster spp., *Dysdercus intermedius, Piesma quadrata, Cimex lectularius, Rhodnius prolixus* and Triatoma spp.
From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.
From the order of the Lepidoptera, for example, *Pectinophora gossypiella, Bupalus piniarius, Cheimatobia*

*brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Caprocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The agents causing fungal and bacterial diseases include:
Xanthomonas species, such as, for example, *Xanthomonas campestris pv. oryzae;*
Pseudomonas species, such as, for example, *Pseudomonas syringae pv. lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubense;*
Plasmopara species, such as, for example, *Plasmopara viticola;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae* and
Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds.

The agents according to the invention are employed in the form of nails, pegs, spikes, plugs, needles, hollow nails, strips, sheets, films, clamps, tapes, wires, threads, fibres, woven fabrics or knitted fabrics.

These are either forced, pressed or knocked into soft tissue or pushed under carefully detached and raised bark or plant rubbers and covered with the detached bark or plant foliage again.

Application of the shaped articles using one of the commercially available nailing or tacking apparatuses, for example based on compressed air, may be mentioned in particular.

The active compounds include, in particular, insecticides and fungicides.

Insecticides which may be mentioned as preferred are organic phosphorus compounds, such as phosphoric acid esters, carbamates, pyrethroids, urea derivatives, such as benzoylureas, triazines, nitromethylenes and nitroguanidines. Juvenile hormones and juvenoid synthetic compounds, such as, for example, pyriproxyfen, methoprene and hydroprene, may also be mentioned.

The pyrethoids include:
Allethrin=2-methyl-4-oxo-3-(2-propenyl)-2-cyclopenten-1-yl 2,2-dimethyl-3-(2-methyl-1-propenyl)-cyclopropane-carboxylate.
Barthrin=(6-chloro-1,3-benzodioxol-5-yl)-methyl 2,2-dimethyl-3-(2-methyl-1-propenyl)-cyclopropane-carboxylate.

Bioresmethrin=[5-(phenyl-methyl)-3-furanyl]-methyl 2,2-dimethyl-3-(2-methyl-1-propenyl)-cyclopropane-carboxylate.

Bromethrin=(5-benzyl-3-furyl)-methyl 2-(2,2-dibromo-vinyl)-3,3-dimethylcyclopropane-carboxylate.

Cycloethrin=3-(2-cyclopenten-1-yl)-2-methyl-4-oxo-2-cyclopenten-1-yl 2,2-dimethyl-3-(2-methyl-propenyl)-cyclopropane-carboxylate.

Dimethrin=2,4-dimethylbenzyl 2,2-dimethyl-3-(2-methyl-1-propenyl)-cyclopropane-carboxylate.

Pyresmethrin=(5-benzyl-3-furyl)-methyl trans-(+)-3-(2-methoxycarbonyl-1-propenyl)-2,2-dimethylcyclopropanecarboxylate.

Resmethrin=(5-benzyl-3-furyl)-methyl 2,2-dimethyl-3-(2-methyl-1-propenyl)-cyclopropane-carboxylate.

Tetramethrin=(1,3,4,5,6,7-hexahydro-1,3-di-oxo-2H-isoindol-2-yl)-methyl 2,2-dimethyl-3-(2-methyl-1-propenyl)-cyclopropane-carboxylate.

K-othrin=α-cyano-3-phenoxybenzyl cis-3-(2,2-dibromovinyl) 2,2-dimethylcyclopropane-carboxylate.

Permethrin (FMC 33297) (NRDC 143)=cis-trans-(+)-m-phenoxybenzyl 3-(2,2-dichlorovinyl)-2,2-dimethyl-cyclopropane-carboxylate.

Cinerin I=2-(2-butenyl)-4-hydroxy-3-methyl-2-cyclopenten-1-one 2,2-dimethyl-3-(2-methyl-1-propenyl)-cyclopropane-carboxylate.

Pyrethrin I=4-hydroxy-3-methyl-2-(2,4-pentadienyl)-2-cyclopenten-1-one 2,2-dimethyl-3-(2-methyl-1-propenyl)-cyclopropane-carboxylate.

Cinerin II=2-(2-butenyl)-4-hydroxy-3-methyl-2-cyclopenten-1-one 2,2-dimethyl-3-(2-methyl-1-propenyl)-cyclopropane-carboxylate.

Pyrethrin II=4-hydroxy-3-methyl-2-(2,4-pentadienyl)-2-cyclopenten-1-one 2,2-dimethyl-3-(2-methyl-1-propenyl)-cyclopropane-carboxylate.

Jasmolin I=4',5'-dihydropyrethrin I.

Jasmolin II=4',5'-dihydropyrethrin II.

Biothanometrin=(5-benzyl-3-furyl)-methyl 2,2-dimethyl-3-(2-cyclopentylvinyl)-cyclopropane-carboxylate.

Bioethanomethrin=(3-diphenyl ether)-methyl 2-(2,2-dichlorovinyl)-3,3-dimethyl-cyclopropane-carboxylate.

Cypermethrin=(3-diphenyl ether)-cyanomethyl 2-(2,2-dichlorovinyl)-3,3-dimethyl-cyclopropane-carboxylate.

Decamethrin=(3-diphenyl ether)-cyanomethyl 2-(2,2-dibromovinyl)-3,3-dimethyl-cyclopropane-carboxylate.

ES-56=2,3-dihydrofuran 2,2-dimethyl-3-(2-methyl-1-propenyl)-cyclopropane-carboxylate.

Fenpropanate (S-3206)=(3-diphenyl ether)-cyanomethyl 2,2-dimethyl-3,3-dimethyl-cyclopropane-carboxylate.

Fenvalerate (S-5602)=(3-diphenyl ether)-cyanomethyl [(p-chlorophenyl)-(isopropyl)]-acetate.

. . . (S-5439)=3-diphenyl ether)-methyl [(p-chlorophenyl)-(isopropyl)-acetate.

Cismethrin=5-benzyl-3-furylmethyl 2,2-dimethyl-3-(2-methyl-1-propenyl)-cyclopropane-carboxylate.

Phenomethrin=(3-phenoxyphenyl)-methyl 2,2-dimethyl-3-(2-methyl-1-propenyl)-cyclopropane-carboxylate.

Cyfluthrin=4-fluoro-3-(diphenyl ether)-cyanomethylol 2-(2,2-dichlorovinyl)-3,3-dimethylcyclopropane-carboxylate.

The carbamates include:

Aldicarb=2-methyl-2-(methylthio)-propanal O-[(methylamino)carbonyl]oxime.

Aldoxycarb=2-methyl-2-(methylsulphonyl)propanal O-[(methylamino)carbonyl]oxime.

Aminocarb=4-dimethylamino-3-methylphenyl methylcarbamate.

Bendiocarb=2,2-dimethyl-benzo-1,3-dioxol-4-yl N-methylcarbamate.

Bufencarb=3-(1-methylbutyl)phenyl methylcarbamate and 3-(1-ethylpropyl)-phenyl methylcarbamate (3:1).

Butacarb=3,5-bis-(1,1-dimethylethyl)phenyl methylcarbamate.

Butocarboxime=3-methylthio-2-butane O-((methylamino)-carbonyl]oxime.

Butoxycarboxime=3-methylsulphonyl-2-butanone O-[(methylamino)carbonyl]oxime.

2-sec-Butylphenyl methylcarbamate=2-(1-methylpropyl)-phenyl methylcarbamate.

Carbanolate=2-chloro-4,5-dimethylphenyl methylcarbamate.

Carbaryl=1-naphthalenyl methylcarbamate.

Carbofuran=2,3-dihydro-2,2-dimethyl-7-benzofuranyl methylcarbamate.

Cartap=S,S'-[2-dimethylamino)-1,3-propanediyl] carbamethioate.

Decarbofuran=2,3-dihydro-2-methylbenzofuran-7-yl methylcarbamate.

Dimetilan=1-[(dimethylamino)carbonyl]-5-methyl-1H-pyrazol-3-yl dimethylcarbamate.

Dioxacarb=2-(1,3-dioxolan-2-yl)phenyl methylcarbamate.

Ethiofencarb=2-ethylthiomethylphenyl methylcarbamate.

Fenethacarb=3,5-diethylphenyl methylcarbamate.

Formetanate=3-dimethylaminoethylenaminophenyl methylcarbamate.

Formparanate=3-methyl-4-dimethylamino-methylenaminophenyl methylcarbamate.

Isoprocarb=2-isopropylphenyl methylcarbamate.

Methiocarb=3,5-dimethyl-4-methylthiophenyl methylcarbamate.

Methomyl=methyl N-[[(methylamino)carbonyl]oxy]-ethanimidothioate.

Mexacarbate=4-dimethylamino-3,5-dimethylphenyl methylcarbamate.

Nabam=disodium 1,2-ethanediylbis(carbamodithioate).

Nitrilacarb=(4,4-dimethyl-5-methylamino-carbonyloximino)pentanenitrile. $ZnCl_2$.

Oxamil=methyl 2-(dimethylamino)-N-[[(methylamino)-carbonyl]oxy]-2-oxoethanimidothioate.

Pirimicarb=2-(dimethylamino)-5,6-dimethyl-4-pyrimidinyl dimethylcarbamate.

Promecarb=3-methyl-5-(1-methylethyl)phenyl methylcarbamate.

Propoxur=2-(1-methylethoxy)phenyl methylcarbamate.

Thiofanox=3,3-dimethyl-(methylthio)-2-butanone O-[(methylamino)carbonyl]oxime.

Thiocarboxim=1-(2-cyanoethylthio)-ethylenaminomethyl carbamate.

Thiram=tetramethylthioperoxy-dicarbonic diamide.

Trimethylphenyl methylcarbamate=3,4,5-trimethylphenyl methylcarbamate.

3,4-Xylylmethylcarbamate=3,4-dimethylphenyl methylcarbamate.

3,5-Xylyl methylcarbamate=3,5-dimethylphenyl methylcarbamate.

The organophosphorus compounds include:

Acephate=O,S-dimethyl acetylphosphoroaminothioate.

Amidithion=S-(N-2-methoxyethylcarbamoylmethyl)-dimethylphosphorodithioate.

Amiton=S-[2-(diethylamino)ethyl] diethyl phosphorothioate.

Athidation=O,O-diethyl S-5-methoxy-2-oxo-1,3,4-thiadiazol-3-yl-methyl phosphorodithioate.

Azinphos-ethyl=O,O-diethyl S-[(4-oxo-1,2,3-benzotriazin-(4H)-yl)methyl] phosphorodithioate.

Azinphos-methyl=O,O-dimethyl S-[(4-oxo-1,2,3-benzotriazin-3(4H)yl)methyl] phosphorodithioate.

Azothoate=O,O-dimethyl O-[p-(p-chlorophenylazo)-phenyl] phosphorothioate.
Bromophos=O-(4-bromo-2,5-dichlorophenyl) O,O-dimethyl phosphorothioate.
Bromophos-ethyl=O-(4-bromo-2,5-dichlorophenyl) O,O-diethyl phosphorothioate.
Butonate=O,O-dimethyl (2,2,2-trichloro-1-hydroxyethyl) phosphonate.
Carbophenothion=S-[(4-chlorophenyl)thio]methyl O,O-diethyl phosphorodithioate.
Chlorfenvinphos=2-chloro-1-(2,4-dichlorophenyl)-ethenyl diethyl phosphate.
Chlormephos=S-chloromethyl O,O-diethyl phosphorodithioate.
Chlorphoxim=7-(2-chlorophenyl)-4-ethoxy-3,5-dioxa-6-aza-4-phosphaoct-6-ene-8-nitrile 4-sulphide.
Chlorprazophos=O,O-diethyl O-3-chloro-7-methyl-pyrazolo[1,5a]pyrimidin-2-yl phosphorothioate.
Chlorpyrifos=O,O-diethyl O-3,5,6-trichloro-2-pyridyl phosphorothioate.
Chlorpyrifos-methyl=O,O-dimethyl O-3,5,6-trichloro-2-pyridyl phosphorothioate.
Chlorthiophos=O-2,5-dichloro-4-(methylthio)-phenyl O,O-diethyl phosphorothioate.
Coumaphos=O-3-chloro-4-methylcouramin-7-yl O,O-diethyl phosphorothioate.
Coumithoate=O,O-diethyl O-(7,8,9,10-tetrahydro-6-oxo-6H-dibenzo[b,d]pyran-3-yl phosphorothioate.
Cortoxyphos=1-phenylethyl (E)-3-[(dimethoxyphosphonyl)-oxy]-2-butenoate.
Crufomate=2-chloro-4-(1,1-dimethylethyl)phenyl methyl methylphosphoramidate.
Cyanofenphos=O-4-cyanophenyl O-ethyl phenylphosphonothioate.
Cyanophos=O-4-cyanophenyl O,O-dimethyl phosphorothioate.
Cyanthoate=O,O-diethyl S-[N-(1-cyano-1-methylethyl)]-carbamoylmethyl phosphorothioate.
Demephion=O,O-dimethyl O-2-methylthioethyl phosphorothioate and O,O-dimethyl S-2-methylthioethyl phosphorothioate.
Demeton=O,O-diethyl O-2-ethylthioethyl phosphorothioate and O,O-diethyl S-2-ethylthioethyl phosphorothioate.
Demeton-S-methyl=O,O-dimethyl S-2-ethylthioethyl phosphorothioate.
Demeton-S-methylsulphone=S-2-ethylsulphonylethyl O,O-dimethyl phosphorothioate.
Demeton-S=O,O-diethyl S-[2-(ethylthio)ethyl] phosphorothioate.
Demeton-O=O,O-diethyl O-[2-(ethylthio)ethyl] phosphorothioate.
Demeton-O-methyl=O,O-dimethyl-O-[2-(ethylthio)ethyl] phosphorothioate.
Dialifos=S-[2-chloro-1-(1,3-dihydro-1,3-dioxy-2H-isoindol-2-yl)ethyl] O,O-diethyl phosphorodithioate.
Diazinon=O,O-diethyl O-[6-methyl-2-(1-methylethyl)-4-pyrimidinyl] phosphorothioate.
Dichlorfenthion=O,O-diethyl O-(2,4-dichlorophenyl) phosphorothioate.
O-2,4-dichlorophenyl O-ethylphenyl phosphonothioate.
Dichlorvos=dimethyl 2,2-dichloroethenyl phosphate.
Dicrotophos=dimethyl 3-(dimethylamino)-1-methyl-3-oxo-1-propenyl phosphate.
Dimefox=bis(dimethylamino)fluorophosphine oxide.
Dimethoate=O,O-dimethyl-S-[2-(methylamino)-2-oxoethyl]phosphorodithioate.
1,3-Di-(methoxycarbonyl)-1-propen-2-yl dimethyl phosphate=dimethyl 3-[(dimethoxyphosphinyl)oxy]-2-pentenedioate.
Dioxathion=S,S'-1,4-dioxane-2,3-diyl O,O,O',O'-tetraethyl di-(phosphorodithioate).
Disulphoton=O,O-dhetyl S-2-ethylthioethyl phosphorodithioate.
EPN=O-ethyl O-4-nitrophenyl phenylphosphonothioate.
Endothion=O,O-dimethyl S-(5-methoxy-4-pyran-2-yl-methyl) phosphorothioate.
Ethion=O,O,O',O'-tetraethyl-S,S'-methylene di(phosphorodithioate).
S-ethylsulphinylmethyl O,O-diisopropyl phosphorodithioate.
Ethoate-methyl=O,O-dimethyl-S-(N-ethylcarbamoyl-methyl) phosphorodithioate.
Ethoprophos=O-ethyl S,S-dipropyl phosphorodithioate.
Etrimfos=O-(6-ethoxy-2-ethyl-4-pyrimidinyl) O,O-dimethyl phosphorothioate.
Famphur=O,O-dimethyl O-p-(dimethylsulphamoyl)-phenyl phosphorothioate.
Fenchlorphos=O,O-dimethyl O-(2,4,5-trichlorophenyl) phosphorothioate.
Fensulphothion=O,O-diethyl O-4-(methylsulphinyl)phenyl phosphorothioate.
Fenthion=O,O-dimethyl O-[3-methyl-4-(methylthio) phenyl] phosphorothioate.
Fonophos=O-ethyl S-phenyl ethylphosphonodithioate.
Formothion=S-[2-(formylmethylamino)-2-oxoethyl] O,O-dimethyl phosphorodithioate.
Fospirate=dimethyl 3,5,6-trichloro-2-pyridyl phosphate.
Fosthietan=diethyl 1,3-dithietan-2-ylidenephosphoramidate.
Heptenophos=7-chlorobicyclo[3,2,0]-hepta-2,6-dien-6-yl dimethyl phosphate.
Iodofenphos=O-2,5-dichloro-4-iodophenyl O,O-dimethyl phosphorothioate.
Isofenphos=1-methylethyl 2-[[ethoxy-[(1-methylethyl)-amino] phosphinothioyl]oxy]benzoate.
Leptophos=O-4-bromo-2,5-dichlorophenyl O-methylphenyl phosphonothioate.
Lythidathion=O,O-dimethyl S-(5-ethoxy-2,3-dihydro-2-oxo-1,3,4-thiadiazol-3-yl-methyl) phosphorodithioate.
Malathion=diethyl (dimethoxyphosphinothioyl) thiobutenedioate.
Mazidox=N,N,N',N'-tetramethylphosphorodiamidic azide.
Mecarbam=ethyl [[(diethoxyphosphinothioyl) thio ] acetyl]-methylcarbamate.
Mecarphon=N-methylcarbonyl-N-methyl-carbamoyl-methyl O-methyl methylphosphonodithioate.
Menazon=S-[(4,6-diamino-1,3,5-triazin-2-yl)-methyl] O,O-dimethyl phosphorodithioate.
Mephosfolan=diethyl 4-methyl-1,3-dithiolan-2-ylidenephosphoroamidate.
Methamidophos=O,S-dimethyl phosphoramidothioate.
Methidathion=S-[[5-methoxy-2-oxo-1,3,4-thiadiazol-3 (2H)-yl]methyl] O,O-dimethyl phosphorodithioate.
Methocrotophos=dimethyl cis-2-(N-methoxy-N-methyl)-carbamoyl)-1-methylvinyl phosphate.
The 2-sulphide of 2-methoxy-4H-benzo-1,3,2-dioxaphosphorin.
Methyl carbophenotion=S-[[(4-chlorophenyl)thio]-methyl] O,O-dimethyl phosphorodithioate.
Mevinphos=methyl 3-[(dimethoxyphosphinyl)oxy]-2-butenoate.
Monocrotophos=dimethyl 1-methyl-3-(methylamino)-3-oxo-1-propenyl phosphate.
Morphothion=O,O-dimethyl S-(morpholino-carbonylmethyl) phosphorodithioate.
Naled=dimethyl 1,2-dibromo-2,2-dichloroethyl phosphate.

Omethoate=O,O-dimethyl S-[2-(methylamino)-2-oxoethyl] phosphorothioate.
Oxydemeton-methyl=S-[2-(ethylsulphinyl)ethyl] O,O-dimethyl phosphorothioate.
Oxydisulphoton=O,O-diethyl S-[2-(ethyl-sulphinyl)-ethyl] phosphorodithioate.
Parathion=O,O-diethyl O-4-nitrophenyl phosphorothioate.
Parathion-methyl=O,O-dimethyl O-4-nitrophenyl phosphorothioate.
Phenkapton=O,O-diethyl S-(2,5-dichlorophenylthiomethyl) phosphorodithioate.
Phenthoate=ethyl α-[(dimethoxyphosphinothioyl)thio]-benzene-acetate.
Phorate=O,O-diethyl S-ethylthiomethyl phosphorodithioate.
Phosalone=S-[(6-chloro-2-oxo(2H)-benzoxazolyl]methyl] O-diethyl phosphorodithioate.
Pholan=diethyl 1,3-dithiolan-2-ylidene phosphoramidate.
Phosmet=S-[(1,3-dihydro-1,3-dioxo-2H-isoindol-2-yl)-methyl] O,O-dimethyl phosphorodithioate.
Phosnichlor=O,O-dimethyl O-4-chloro-3-nitrophenyl phosphorothioate.
Phosphamidon=2-chloro-3-(diethylamino)-1-methyl-3-oxo-1-propenyl dimethyl phosphate.
Phoxim=α-[[diethoxyphosphinothioyl)oxy]imino]-benzeneacetonitrile.
Pirimiphos-ethyl=O-[2-(diethylamino)-6-methyl-4-pyrimidinyl] O,O-diethyl phosphorothioate.
Pirimiphos-methyl=O-[2-(diethylamino)-6-methyl-4-pyrimidinyl] O,O-dimethyl phosphorothioate.
Profenofos=O-(4-bromo-2-chlorophenyl) O-ethyl S-propyl phosphorothioate.
Propetamphos=(E)-1-methylethyl 3-[[(ethylamino)-methoxyphosphinothioyl]oxy]-2-butenoate.
Prothidathion=O,O-diethyl S-(2,3-dihydro-5-isopropyl-2-oxo-1,3,4-thiadiazol-3-yl-methyl) phosphorodithioate.
Prothoate=O,O-diethyl S-[2-(1-methylethyl)amino-2-oxoethyl] phosphorodithioate.
Quinalphos=O,O-diethyl O-2-quinoxalinyl phosphorothioate.
Quinothion=O,O-diethyl 2-methylquinolin-4-yl phosphorothioate.
Quintiofos=O-ethyl O-8-quinolinoyl phenylphosphonothioate.
Sophamide=O,O-dimethyl S-(N-methoxy-methyl)-carbamoylmethyl phosphorodithioate.
Sulfotepp=tetraethyl thiodiphosphate.
Sulprofos=O-ethyl O-(4-methylthiophenyl) S-propyl phosphorodithioate.
Temephos=O,O'-(thiodi-4,1-phenylene) O,O,O',O'-tetramethyl di(phosphorodithioate).
Tepp=tetraethyl diphosphate.
Terbufos=S-[(1,1-dimethylethyl)thiomethyl] O,O-diethyl phosphorodithioate.
Tetrachlorvinphos=dimethyl trans-2-chloro-1-(2,4,5-trichlorophenyl)vinyl phosphate.
O,O,O',O'-tetrapropyl dithiopyrophosphate=tetrapropyl thiodiphosphate.
Thiometon=O,O-dimethyl S-[2-(ethylthio)ethyl] phosphorodithioate.
Thionazin=O,O-diethyl O-pyrazinyl phosphorothioate.
Triazophos=O,O-diethyl O-(phenyl-1H-1,2,4-triazol-3-yl) phosphorothioate.
Trichloronat=O-ethyl O-2,4,5-trichlorophenyl ethylphosphonothioate.
Trichlorphon=dimethyl 1-hydroxy-2,2,2-trichloroethyl phosphonate.

Vamidothion=O,O-dimethyl S-[2-(1-methylcarbamoylethyleneethyl] phosphorothioate.

The benzoylureas include compounds of the formula:

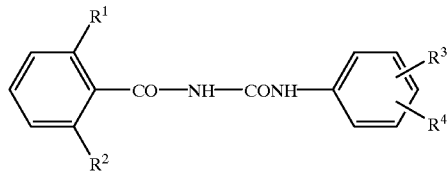

wherein $R^1$ represents halogen, $R^2$ represents hydrogen or halogen, $R^3$ represents hydrogen, halogen or $C_{1-4}$-alkyl and $R_4$ represents halogen, 1–5-halogen-$C_{1-4}$-alkyl, $C_{1-4}$-alkoxy, 1–5-halogeno-$C_{1-4}$-alkoxy, $C_{1-4}$-alkylthio, 1–5-halogeno-$C_{1-4}$-alkylthio phenoxy or pyridyloxy which can optionally be substituted by halogen, $C_{1-4}$-alkyl, 1–5-halogeno-$C_{1-4}$-alkyl, $C_{1-4}$-alkoxy, 1–5-halogeno-$C_{1-4}$-alkoxy, $C_{1-4}$-alkylthio, 1–5-halogeno-$C_1$–$C_4$-alkylthio.

Benzoylureas which may be mentioned in particular are those of the formula:

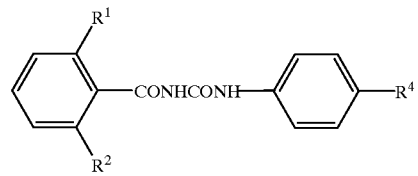

| $R^1$ | $R^2$ | $R^4$ |
|---|---|---|
| H | Cl | $CF_3$ |
| Cl | Cl | $CF_3$ |
| F | F | $CF_3$ |
| H | F | $CF_3$ |
| H | Cl | $SCF_3$ |
| F | F | $SCF_3$ |
| H | F | $SCF_3$ |
| H | Cl | $OCF_3$ |
| F | F | $OCF_3$ |
| H | F | $OCF_3$ |
| F | F | 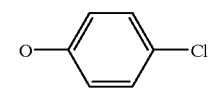 |
| F | F | 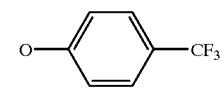 |
| F | F |  |

The triazines include compounds of the formula

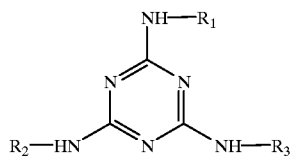

wherein
R₁ represents cyclopropyl or isopropyl;
R₂ denotes hydrogen, halogen, $C_1$-$C_{12}$-alkylcarbonyl, cyclopropylcarbonyl, $C_1$-$C_{12}$-alkylcarbamoyl, $C_1$-$C_{12}$-alkylthiocarbamoyl or $C_2$-$C_6$-alkenylcarbamoyl; and
R₃ represents hydrogen, $C_1$-$C_{12}$-alkyl, cyclopropyl, $C_2$-$C_6$-alkenyl, $C_1$-$C_{12}$-alkylcarbonyl, cyclopropylcarbonyl, $C_1$-$C_{12}$-alkylcarbamoyl, $C_1$-$C_{12}$-alkylthiocarbamoyl or $C_2$-$C_6$-alkenylcarbamoyl, and acid addition salts thereof which are non-toxic to warm-blooded animals.
Compounds which may be mentioned in particular are:

| R₁ | R₂ | R₃ |
|---|---|---|
| Cyclopropyl | H | H |
| Cyclopropyl | H | CH₃ |
| Cyclopropyl | H | C₂H₅ |
| Cyclopropyl | H | C₃H₇-n |
| Cyclopropyl | H | C₄H₉-n |
| Cyclopropyl | H | C₅H₁₁-n |
| Cyclopropyl | H | C₆H₁₃-n |
| Cyclopropyl | H | C₇H₁₅-n |
| Cyclopropyl | H | C₈H₁₇-n |
| Cyclopropyl | H | C₁₂H₂₅-n |
| Cyclopropyl | H | CH₂-C₄H₉-t |
| Cyclopropyl | H | CH₂CH(CH₃)C₂H₅ |
| Cyclopropyl | H | CH₂CH=CH₂ |
| Cyclopropyl | Cl | C₂H₅ |
| Cyclopropyl | Cl | C₆H₁₃-n |
| Cyclopropyl | Cl | C₈H₁₇-n |
| Cyclopropyl | Cl | C₁₂H₅-n |
| Cyclopropyl | H | Cyclopropyl |
| Cyclopropyl | H | COCH₃ |
| Cyclopropyl | H | COCH₃HCl |
| Cyclopropyl | H | COC₂H₅ · HCl |
| Cyclopropyl | H | COC₂H₅ |
| Cyclopropyl | H | COC₃H₇-n |
| Cyclopropyl | H | COC₃H₇-i |
| Cyclopropyl | H | COC₄H₉-t · HCl |
| Cyclopropyl | H | COC₄H₉-n |
| Cyclopropyl | H | COC₆H₁₃-n |
| Cyclopropyl | H | COC₁₁H₂₃-n |
| Cyclopropyl | COCH₃ | COC₂H₅ |
| Cyclopropyl | COC₃H₇-n | COC₆H₁₃-n |
| Cyclopropyl | COCH₃ | COC₃H₇-n |
| Cyclopropyl | COC₂H₅ | COC₃H₇-n |
| Cyclopropyl | H | COCyclopropyl |
| Cyclopropyl | COCy: cyclopropyl | COCyclopropyl |
| Cyclopropyl | COCH₃ | COCH₃ |
| Isopropyl | H | H |
| Isopropyl | H | COCH₃ |
| Isopropyl | H | COC₃H₇-n |
| Cyclopropyl | H | CONHCH₃ |
| Cyclopropyl | H | CONHC₃H₇-i |
| Cyclopropyl | CONHCH₃ | CONHCH₃ |
| Cyclopropyl | H | CSNHCH₃ |
| Cyclopropyl | H | CONHCH₂CH=CH₂ |
| Cyclopropyl | CONHCH₂CH=CH₂ | CONHCH₂CH=CH₂ |
| Cyclopropyl | CSNHCH₃ | CSNHCH₃ |

The nitromethylenes and nitroguanidines and cyanimides include compounds which can preferably be summarised under the general formula I

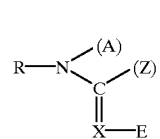

in which
R represents hydrogen or optionally substituted acyl, alkyl, aryl, aralkyl, heteroaryl or heteroarylalkyl radicals;
A represents a monofunctional group from the series comprising hydrogen, acyl, alkyl and aryl, or represents a bifunctional group, which is linked to the radical Z;
E represents an electron-withdrawing group, such as, for example, NO₂ or CN;
X represents the radicals —CH= or =N—, wherein the radical —CH= can be linked to the radical Z instead of an H atom; and
Z represents a monofunctional group from the series comprising alkyl, —O—R, —S—R or

or represents a bifunctional group, which is linked to the radical A or the radical X.
Particularly preferred compounds of the formula are those in which the radicals having the following meaning:
R represents hydrogen, or represents optionally substituted radicals from the series comprising acyl, alkyl, aryl, aralkyl, heteroaryl and heteroarylalkyl.
Acyl radicals which may be mentioned are formyl, alkylcarbonyl, arylcarbonyl, alkylsulphonyl, arylsulphonyl and (alkyl)- or (aryl)-phosphoryl, which can in turn be substituted.
Alkyl which may be mentioned is $C_{1-10}$-alkyl, in particular $C_{1-4}$-alkyl, specifically methyl, ethyl, i-propyl or sec- or t-butyl, which can in turn be substituted.
Aryl which may be mentioned is phenyl or naphthyl, in particular phenyl.
Aralkyl which may be mentioned is phenylmethyl or phenethyl.
Heteroaryl which may be mentioned is heteroaryl having up to 10 ring atoms and N, O or S, in particular N, as hetero atoms. Radicals which may be mentioned specifically are thiophenyl, furyl, thiazolyl, imidazolyl, pyridyl and benzothiazolyl.
Heteroarylalkyl which may be mentioned is heteroarylmethyl, or heteroarylethyl having up to 6 ring atoms and N, O and S, in particular N, as hetero atoms.
Substituents which may be mentioned as examples and as preferred are:
alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different and preferred halogen atoms being fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2, carbon atoms per alkyl group, such as methylamino, methylethyl-amino, n- and i-propylamino and methyl-n-butylamino; carboxyl; carbalkoxy having preferably 2 to 4, in particular 2 or 3, carbon atoms, such as carbomethoxy and carboethoxy; sulpho(—SO₃H); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl; and heteroarylamino and heteroarylalkylamino, such as chloropyridylamino and chloropyridylmethylamino.

A represents hydrogen or optionally substituted radicals from the series comprising acyl, alkyl and aryl, which preferably have the abovementioned meanings. A furthermore represents a bifunctional group. Optionally substituted alkylene having 1 to 4, in particular 1–2, C atoms, substituents which may be mentioned being the substituents listed above, may be mentioned.

A and Z, together with the atoms to which they are bonded, can form a saturated or unsaturated heterocyclic ring. The heterocyclic ring can contain a further 1 or 2 identical or different hetero atoms and/or hetero groups. Preferred hetero atoms are oxygen, sulphur or nitrogen, and hetero groups are N-alkyl, the alkyl of the N-alkyl group preferably containing 1 to 4, in particular 1 or 2, carbon atoms. Methyl, ethyl, n- and i-propyl and n-, i- and t-butyl may be mentioned as alkyl. The heterocyclic ring contains 5 to 7, preferably 5 or 6, ring members.

Examples of the heterocyclic ring which may be mentioned are imidazolidine, tetrahydropyrimidine, thiazolidine, 2H-thiazine, hexahydro-1,3,5-triazine, pyrrolidine, piperidine, piperazine, hexymethyleneimine, morpholine and N-methylpiperazine.

E represents an electron-withdrawing radical, $NO_2$ CN, halogenoalkylcarbonyl, such as 1–5-halogeno-$C_{1-4}$-carbonyl, especially $COCF_3$, being mentioned in particular. p1 X represents —CH= or —N=.

Z represents optionally substituted alkyl, —OR, —SR or —NRR radicals, wherein R and the substituents preferably have the abovementioned meaning.

Z, together with the atom to which it is bonded and the radical in the position of X, can form a saturated or unsaturated heterocyclic ring. The heterocyclic ring can contain a further 1 or 2 identical or different hetero atoms and/or hetero groups.

Preferred hetero atoms are oxygen, sulphur or nitrogen, and hetero groups are N-alkyl, the alkyl of the N-alkyl group preferably containing 1 to 4, in particular 1 or 2, carbon atoms. Methyl, ethyl, n- and i-propyl and n-, i- and t-butyl may be mentioned as alkyl. The heterocyclic ring contains 5 to 7, preferably 5 or 6, ring members.

Examples of the heterocyclic ring which may be mentioned are imidazolidine, tetrahydropyrimidine, thiazolidine, 2H-thiazine, hexahydro-1,3,5-triazine, pyrrolidine, piperidine, piperazine, hexymethyleneimine, morpholine and N-methylpiperazine.

Compounds which may be mentioned as compounds which can especially preferably be used according to the invention are those of the general formulae II and III:

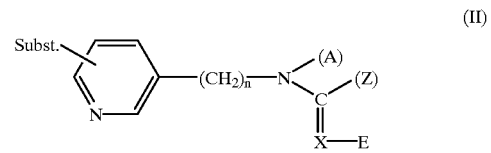

in which n represents 1 or 2,

Subst. represents one of the abovementioned substituents, in particular halogen, especially chlorine, and A, Z, X and E have the abovementioned meanings,

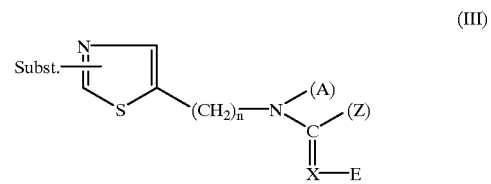

in which the radicals have the abovementioned meaning.

The following compounds may be mentioned specifically:

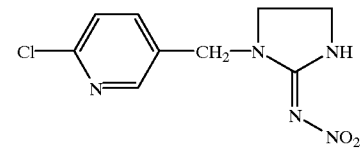

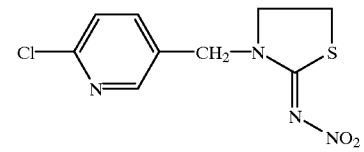

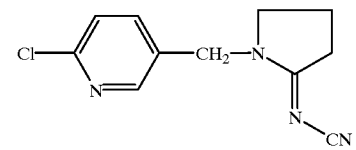

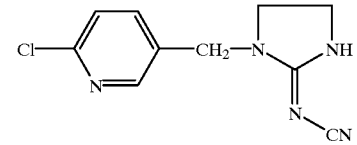

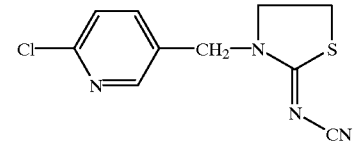

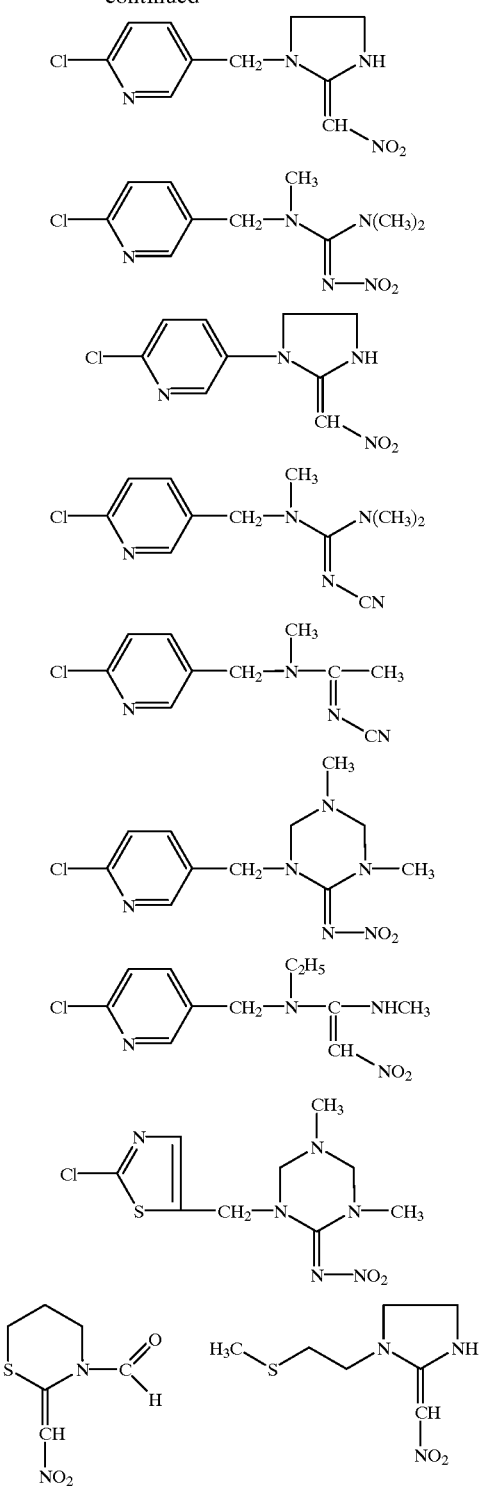

These compounds are agonists or antagonists of the nicotinergic acetylcholine receptors of insects, and are known as such from the following publications:

European Published Specifications No. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372 and 302 389;

German Offenlegungsschriften No. 3 639 877 and 3 712 307;

Japanese Published Specifications No. 03 220 176, 02 207 083, 63 307 857, 63 287 764, 03 246 283, 04 9371, 03 279 359 and 03 255 072;

U.S. Pat. Nos. 5,034,524, 4,948,798, 4,918,086, 5,039, 686 and 5,034,404;

PCT Applications No. WO 91/17 659 and 91/4965;

French Application No. 2 611 114; and

Brazilian Application No. 88 03 621.

Reference is expressly made here to the generic formulae and definitions described in these publications and to the individual compounds described therein.

Preferred fungicides which may be mentioned are:

Sulfenamides, such as dichlorfluanid (Euparen), tolylfluanid (Methyleuparen), folpet and fluorfolpet;

benzimidazoles, such as carbendazim (MBC), benomyl, fuberidazole, thiabendazole or salts thereof;

thiocyanates, such as thiocyanatomethylthiobenzothiazole (TCMTB) and methylene bisthiocyanate (MBT);

quaternary ammonium compounds, such as benzyldimethyltetradecylammonium chloride, benzyl-dimethyl-dodecyl-ammonium chloride and dodecyl-dimethyl-ammonium chloride; morpholine derivatives, such as $C_{11}$–$C_{14}$-4-alkyl-2,6-dimethyl-morpholine homologues (tridemorph), (±)-cis-4-(3-tert.-butylphenyl)-2-methylpropyl]-2,6-dimethylmorpholine (fenpropimorph) and falimorph;

phenols, such as o-phenylphenol, tribromophenol, tetrachlorophenol, pentachlorophenol, 3-methyl-4-chlorophenol, di-chlorophen, chlorophen or salts thereof;

azoles, such a triadimefon, triadimenol, bitertanol, tebuconazole, propiconazole, azaconazole, hexaconazole, prochloraz, cyproconazole, 1-(2-chlorophenyl)-2-(1-chlorocyclopropyl)-3-(1,2,4-triazol-1-yl)-propan-2-ol and 1-(2-chlorophenyl)-2-(1, 2,4-triazol-1-yl-methyl)-3,3-dimethyl-butan-2-ol.

Iodopropargyl derivatives, such as iodopropargyl butyl-carbamate (IPBC), chlorophenylformal, phenylcarbamate, hexylcarbamate and cyclohexylcarbamate and iodopropargyloxyethyl phenylcarbamate;

iodine derivatives, such as diiodomethyl-p-arylsulphones, for example diiodomethyl-p-tolyl-sulphone;

bromine derivatives, such as bromopol;

isothiazolines, such as N-methylisothiazolin-3-one, 5-chloro-N-methylisothiazolin-3-one, 4,5-dichloro-N-octyl-isothiazolin-3-one, N-octylisothiazolin-3-one (octilinone);

benzisothiazolinones and cyclopentene-isothiazolines;

pyridines, such as 1-hydroxy-2-pyridinethione and tetrachloro-4-methylsulphonylpyridine;

nitrites, such as 2,4,5,6-tetrachloroisophthalonitrile (chlorothalonil) and the like, and microbicides having an activated halogen group, such as Cl—Ac, MCA, tectamer, bromopol and bromidox;

benzothiazoles, such as 2-mercaptobenzothiazoles; . . . dazomet; and quinolines, such as 8-hydroxyquinoline.

Insecticides which may be mentioned as particularly preferred are:

phosphoric acid esters, such as azinphos-ethyl, azinphos-methyl, 1-(4-chlorophenyl)-4-(O-ethyl-S-propyl)

phosphoryloxypyrazole (TIA-230), chlorpyrifos, coumaphos, demeton, demeton-S-methyl, diazinon, dichlorvos, dimethoate, ethoprophos, etrimfos, fenitrothion, fention, heptenophos, parathion, parathion-methyl, phosalone, phoxion, pirimiphos-ethyl, pirimiphos-methyl, profenofos, prothiofos, sulprofos, triazophos and trichlorphon.

Carbamates, such as aldicarb, bendiocarb, BPMC (2-(1-methylpropyl)phenyl methylcarbamate), butocarboxime, butoxycarboxime, carbaryl, carbofuran, carbosulphan, cloethocarb, isoprocarb, methomyl, oxamyl, pirimicarb, promecarb, propoxur and thiodicarb.

Pyrethroids, such as allethrin, alphamethrin, bioresmethrin, byfenthrin, (FMC 54 800), cycloprothrin, cyfluthrin, decamethrion, cyhalothrin, cypermethrin, deltamethrin, alpha-cyano-3-phenyl-2-methylbenzyl 2,2-dimethyl-3-(2-chloro-2-trifluoromethylvinyl)cyclopropanecarboxylate, fenpropathrin, fenfluthrin, fenvalerate, flucythrinate, flumethrin, fluvalinate, permethrin and resmethrin; and nitroimino and nitroimides, such as 1-[(6-chloro-3-pyridinyl)-methyl]-4,5-dihydro-N-nitro-1H-imidazol-2-amine (imidacloprid).

Substances forming the matrix of a solid carrier are solid degradable organic substances such as solid fatty acids and their salts, solid fats, waxes, solid paraffins, solid surface active agents and bentonite and furthermore polymeric carrier materials. Preferred are polymeric carrier materials.

Polymeric carrier materials which may be mentioned are:

all the polymers which can be used for the preparation of plastics moulding compositions, such as, for example, polyolefins, such as polyethylene, polyisobutylene and polypropylene; vinyl polymers, such as polyvinyl chloride (PVC), polyvinyl acetate, polyvinyl alcohol, polystyrene and polyacrylonitrile; polyacrylates and polymethacrylates; polyacetals; polycondensates and polyadducts, such as polyamides, polyesters, polyurethanes, polycarbonates and polyalkylene terephthalates; polyaryl ethers and polyimides, as well as high molecular weight polyalkylene oxides, such as homo- and copolymers of ethylene oxide and propylene oxide, polyalkylenoxidalkylethers or polyalkylenoxidealkylarylethers.

Polymers which may furthermore be mentioned are copolymers of olefin/vinyl esters, such as ethylene/vinyl acetate copolymers; ethylene/vinyl alcohol copolymers; olefin/acrylate and methacrylate copolymers, such as ethylene/acrylic acid copolymers, ethylene/ethyl acrylate copolymers and ethylene/methyl acrylate copolymers; and ABS copolymers, styrene/acrylonitrile copolymers, styrene/butadiene copolymers and olefin/maleic anhydride copolymers, such as ethylene/maleic anhydride copolymers.

Polymeric carrier materials which can furthermore be used are:

starch polymers, such as natural starch, amylose and starch polymer/thermoplastic mixtures; sugar polymers, such as polymaltoses; and celluloses and cellulose derivatives, such as cellulose esters, cellulose ethers and cellulose nitrate.

Polyoxyalkylated celluloses, starches and lignin sulfonates. Hydrogels, such as alginates.

Naturally occurring resins, such as colophony, gum Arabic and agar—agar.

Polymeric carrier materials which may furthermore be mentioned are thermoplastic elastomers. These are materials which contain elastomeric phases either physically mixed into or chemically bonded in polymers which can be processed as thermoplastics. A distinction is made between polyblends, in which the elastomeric phases are present in physically mixed-in form, and block copolymers, in which the elastomeric phases are a constituent of the polymeric matrix. As a result of the build-up of the thermoplastic elastomers, hard and soft regions are present side by side. The hard regions here form a crystalline network structure or a continuous phase, the intermediate spaces of which are filled by elastomeric segments. Because of this build-up, these materials have rubber-like properties.

A distinction is made between 5 main groups of the thermoplastic elastomers which may be mentioned as preferred at this point:

1. Copolyesters
2. Polyether block amides (PEBA)
3. Thermoplastic polyurethanes (TPU)
4. Thermoplastic polyolefins (TPO)
5. Styrene block copolymers.

Mixtures of the polymers mentioned can of course also be used as the polymeric carrier materials.

Preferred polymeric carrier materials are polymers which can be processed as thermoplastics and have processing temperatures of 50–260° C., particularly preferably 50–200° C.

Polymers which can be degraded via photochemical processes, such as ethylene/CO copolymers, vinyl ketone copolymers and polymers containing additives which initiate photodegradation, are furthermore preferred.

Particularly preferred polymers are those from the group of biodegradable polymers, such as starch polymers and starch polymer/thermoplastic mixtures; sugar polymers; celluloses and cellulose derivatives; polyoxyalkylated celluloses and starches; hydrogels, such as alginates; naturally occurring resins, such as colophony, gum Arabic and agar-agar; homo- and copolymers of lactic acid, such as polylactides and polylactide glycolides, as well as polyglycolides. Poly-e-caprolactone and polymers from the group comprising polyhydroxyalkanoates, such as poly-3-hydroxybutyric acid (PHB) and copolymers of 3-hydroxybutyric with 3-hydroxyvaleric acid (PHBV), are especially preferred.

Polymers from the group of polycondensates which are particularly suitable are polyamides and/or polyesters having a melting or softening point of 50–160° C. From the substance class of polyamides, those which are preferred are homopolyamides and/or copolyamides of ω-aminocaproic acid, ω-aminooenanthic acid, ω-aminocaprylic acid, ω-aminopelargonic acid, ω-aminocapric acid, ω-aminoundecylic acid, ω-aminolauric acid and/or caprolactam, lactam-7, lactam-8, lactam-9, lactam-10, lactam-11 or lauryllactam, and/or of dimethylenediamine, trimethylenediamine, tetramethylenediamine, pentamethylenediamine, hexamethylenediamine, polyetherdiamine and oxalic acid, malonic acid, succinic acid, glutaric acid, adipic acid, pimelic acid, suberic acid, azelaic acid, sebacic acid, nonanedicarboxylic acid, decanedicarboxylic acid, undecanedicarboxylic acid, dodecanedicarboxylic acid and dimerised fatty acid.

Those of caprolactam, lauryllactam, ω-aminolauric acid, ω-aminocaproic acid, hexamethylenediamine, polyether-diamine, adipic acid, dimerised fatty acid or mixtures thereof are particularly preferred.

From the substance class of polyesters, homopolyesters and/or copolyesters of ω-hydroxyacetic acid, ω-hydroxypropionic acid, ω-hydroxybutyric acid, ω-hydroxyvaleric acid, ω-hydroxycaproic acid, ω-hydroxyoenanthic acid, ω-hydroxycaprylic acid, ω-hydroxypelargonic acid, ω-hydroxycapric acid, ω-hydroxyundecylic acid, ω-hydroxylauric acid and/or caprolactone, lactone-7, lactone-8, lactone-9, lactone-10, lactone-11, lauryllactone and/or ethylene glycol, propanediol, butanediol, pentanediol, hexanediol, an aliphatic diol mixture having 2 to 18 C atoms and oxalic acid, malonic acid, succinic acid, glutaric acid, adipic acid, pimelic acid, suberic acid, azelaic acid, sebacic acid, nonanedicarboxylic acid, decanedicarboxylic acid, undecanedicarboxylic acid, dodecanedicarboxylic acid, terephthalic acid, isophthalic acid and/or anhydrides thereof and/or chlorides thereof and/or esters thereof are preferred.

Preferred polymeric carrier materials are formed from polyurethanes. Polyurethanes are prepared in a manner which is known per se by reaction of polyisocyanates with higher molecular weight compounds which contain at least two groups which are reactive towards isocyanates, and if appropriate low molecular weight chain-lengthening agents and/or monofunctional chain stoppers (see, for example, S. H. Saunders, K. C. Frisch; Polyurethanes, Part I, High Polymer Science XVI, Interscience Publishers, New York 1962).

Preferred polyisocyanates are in general the toluylene diisocyanates and the diphenylmethane diisocyanates.

It is of course possible to use mixtures of the abovementioned compounds having at least two hydrogen atoms which are reactive towards isocyanates and a molecular weight of 400 to 10 000, for example mixtures of polyethers and polyesters.

Possible starting components for polyurethane polymerisation which are optionally to be enjoyed are also compounds having at least two hydrogen atoms which are reactive towards isocyanates and a molecular weight of 32 to 400. In this case also, this is understood as meaning compounds containing hydroxyl groups and/or amino groups and/or thiol groups and/or carboxyl groups, preferably compounds containing hydroxyl groups and/or amino groups, which serve as chain-lengthening agents or crosslinking agents. These compounds as a rule have 2 to 8 hydrogen atoms which are reactive towards isocyanates, preferably 2 or 3 reactive hydrogen atoms.

Photodegradable polymers are polymers which contain groups which are sensitive to UV light and/or additives which initiate photochemical reactions.

Polymers containing groups which are sensitive to UV light which may be mentioned are the copolymers of ethylene and carbon monoxide prepared by free radical polymerisation, such as are described, for example, in U.S. Pat. No. 2,495,286 and DE 2,316,697 and U.S. Pat. No. 3,921,144. The copolymers, described, for example, in U.S. Pat. Nos. 3,759,952, 3,811,931, 385,814, 3,860,538 and 3,878,169, of vinyl monomers containing keto groups, such as methyl vinyl ketone, methyl isopropenyl ketone and ethyl vinyl ketone, with, for example, polyolefins, such as ethylene, propylene and vinyl compounds, such as styrene and methyl methacrylate, may furthermore be mentioned. Such products are obtainable, for example, under the name $^R$Ecolyte, and can be employed as the polymeric carrier materials either by themselves or, preferably, as a mixture with the corresponding base polymers in amounts of 5–10 parts by weight.

Polymers containing additives as initiators for photodegradation are preferably prepared on the basis of polyolefins, such as polyethylene, polybut-1-ene and vinyl resins, such as polystyrene and PVC. Photoreactive additives are preferably organic carbonyl compounds, such as, for example, aromatic aldehydes, ketones, diketones and quinones. Benzophenone and derivatives thereof are particularly preferred. Another group of preferred photoreactive additives are inorganic and organic salts, such as, for example, chlorides, stearates and octoates, of transition metals, such as, for example, iron, nickel, cobalt, copper and manganese. Organic complexes of transition metals, such as, for example, ferrocenes and, preferably, dithiocarbamates of iron and magnesium are likewise employed.

Of the starch polymers, the starches which can be processed as thermoplastics and the starch polymer/thermoplastic mixtures are preferably suitable as the polymeric carrier materials. They can be employed by themselves and/or as a masterbatch, mixed with the thermoplastics. The thermoplastics preferably comprise amounts of photodegradable polymers.

Starch which can be processed as a thermoplastic is, for example, natural starch containing water as a softener, as described, for example, in EP 0 118 240; destructured starch, as described, for example, in EP 0 304 401 and 0 391 853, and hydroxyalkoxylated starch, such as, for example, hydroxyethyl- and hydroxypropyl-substituted starch. Softener-containing starches having a high amylose content furthermore can be processed as thermoplastics, as mentioned, for example, in DE 4 013 344. Softeners which are preferably employed are polyhydric alcohols, such as, for example, glycerol, diethylene glycol, triethylene glycol, sorbitol, polyvinyl alcohol and citric acid oxide adduct.

The starch polymer/thermoplastic mixtures include the mixtures, comprising 6–15 parts by weight of starch, with, for example, PVC, ethylene/vinyl acetate copolymers, polyurethanes and, preferably, polyolefins, such as polypropylene, and particularly preferably polyethylene, such as are obtainable, for example, by the names Ecostar, Polyclean, Amyplast and Poly-Grade. The starch used for such mixtures with thermoplastics can be surface-modified, for example with silanes, or can be employed as non-modified starch in the dried state. The mixtures can additionally comprise additives. These are, for example, unsaturated compounds, such as unsaturated fatty acid esters, for example soya oil; styrene/butadiene block copolymers; naturally occurring rubber; and organic salts of transition metals, such as, for example, cobalt naphthenate and antioxidants of the known type.

Starch polymer/thermoplastic mixtures having a starch content of up to 95 parts by weight, such as are obtained, for example, by mixing starch with polymers containing carboxyl groups, such as, for example, ethylene/acrylic acid copolymers, furthermore can be used according to the invention.

The preparation of such mixtures from the destructured starch is described, for example, in EP 0 404 727. EP 0 519 367 uses a starch which has been modified chemically by reaction of the OH groups with alkylene oxides and other substances which form ethers, esters, urethanes, carbamates and/or isocyanates for mixing with thermoplastics. Copolyamides, copolyesters and/or polyolefins are preferred. Polyols, such as, for example, glycerol, sorbitol and polyethylene glycol, as softeners, urea and/or urea derivatives and emulsifiers, such as metal stearates, glycerol monostearates and polyoxyethylene fatty acid esters, such as, for example, polyoxyethylene-20 sorbitan monolaurate, can additionally be added to these mixtures.

Starch polymer/thermoplastic mixtures which can be employed according to the invention can also comprise graft copolymers of starch with, for example, maleic anhydride and vinyl monomers, such as, for example, styrene, acrylonitrile and acrylic and methacrylic monomers, for example butyl and methyl methacrylate, as compatibilising agents.

Copolymers such as are obtained in accordance with DE 3,007,433 by polymerisation of ethylene in the presence of starch modified by Ziegler-Natta catalysts furthermore are suitable.

Celluloses and cellulose derivatives, such as, for example, cellulose esters, for example cellulose acetate, cellulose propionate, cellulose butyrate and mixed esters, such as, for example, cellulose acetobutyrate; cellulose ethers, for example methyl-, ethyl- and hydroxyethylcellulose and sodium carboxymethylcellulose, and cellulose nitrate are known and are suitable as polymeric carrier materials.

Preferred substances are derivatives which can be processed as thermoplastics and/or are degradable, such as, for example, the mixtures, described in EP 0 394 803, of cellulose esters, such as cellulose acetate and/or cellulose acetobutyrate, with biodegradable additives, such as carboxylic acid esters having several ester and/or hydroxyl groups, for example esters of citric acid, tartaric acid or succinic acid, as softeners, linear polyesters and, if appropriate, organic acids and/or acid esters which differ from the softener. Organic metal compounds, such as, for example, iron(II) acetylacetonate or bis(cyclopentadienyl)-iron or derivatives thereof, can additionally be contained in the mixture to increase the degradability.

Particularly preferred polymeric carrier materials are cellulose/lactone graft copolymers, such as, for example, cellulose polyhydroxyhexanoate.

Polyhydroxyalkanoates are polymers of aliphatic and aromatic hydroxycarboxylic acids which are formed by prokaryotic microorganisms and can be prepared by means of fermentative processes, such as are described, for example, in EP 0 015 669, 0 046 344 and 0 052 459.

Suitable polyhydroxyalkanoates are, for example, polymers of 4-hydroxybutyric acid, 4-hydroxyvaleric acid and 5-hydroxyvaleric acid; of the 3-hydroxy derivatives of saturated carboxylic acids, such as, for example, propionic acid, butyric acid, valeric acid, hexanoic acid, heptanoic acid, octanoic acid, nonanoic acid, decanoic acid, undecanoic acid, dodecanoic acid, 4-methylhexanoic acid, 5-methylhexanoic acid, 5-methyloctanoic acid, 6-methyloctanoic acid and 7-methyloctanoic acid; of the 3-hydroxy derivatives of unsaturated carboxylic acids, such as, for example, crotonic acid, 4-pentenoic acid, 4-hexenoic acid, 5-hexenoic acid, 6-octenoic acid, 7-octenoic acid, 8-nonenoic acid, 9-decenoic acid, 6-dodecenoic acid, 5-tetradecenoic acid and 5,8-tetradecadienoic acid; and of the 3-hydroxy derivatives of halogenocarboxylic acids, such as 6-bromohexanoic acid, 6-chlorohexanoic acid, 7-fluoroheptanoic acid, 8-bromooctanoic acid, 8-chlorooctanoic acid, 9-fluorononanoic acid and 11-bromoundecanoic acid.

Preferred polymeric carrier materials are homo- and copolymers of 3-hydroxybutyric acid, and copolymers thereof with 3-hydroxyvaleric acid are particularly preferred. Such products are obtainable, for example, under the name $^R$Biopol.

As a further preferred group of carrier materials may be mentioned solid fatty acids such as capric acid, lauric acid, myristic acid, palmitic acid, stearic acid; solid fats; waxes such as spermacetic and carnauba wax; paraffine waxes.

As a further preferred group of carrier materials may be mentioned solid surface active agents such as polyalkylene oxide alkyl or alkyl aryl ether, polyalkylene oxide fatty acid esters, polyalkylene oxide alkyl esters, polyalkylene oxide alkyl amines, poly fatty acid esters, polyalkylene oxide polyol ester ethers, alkylsulfonates, alkyl arylsulfonates, alkyl naphthalene sulfonates, dialkyl sulfosuccinates, polyalkylene alkyl ether sulfates, polyalkylene alkylaryl ether sulfates, poly sulfates, polyalkylene oxide alkyl ether phosphates, polyalkylene oxide alkyl aryl ether phosphates and polyol phosphates. The polymeric material can contain appropriate additives such as plasticizers.

The plasticisers which are usually used for plasticising solid vinyl resins are suitable for production of the shaped articles based on polymers which can be processed as thermoplastics, such as, for example, polyvinyl resins. The plasticiser used depends on the resin and its compatibility with the plasticiser. Examples of suitable plasticiser are esters of phosphoric acid, such as tricresyl phosphate, esters of phthalic acid, such as dimethyl phthalate and dioctyl phthalate, and esters of adipic acid, such as diisobutyl adipate. It is also possible to use other esters, such as the esters of azelaic acid, maleic acid, ricinoleic acid, myristic acid, palmitic acid, oleic acid, sebacic acid, stearic acid and trimellitic acid, as well as complex linear polyesters, polymeric plasticisers and epoxidised soya bean oils. The amount of plasticiser is about 10 to 50% by weight, preferably about 20 to 45% by weight of the total composition.

The shaped articles can also comprise further constituents, such as stabilising agents, lubricants, fillers, surface active agents and colouring agents, without the fundamental properties of the composition thereby being changed. Suitable stabilising agents are antioxidants and agents which protect the shaped article from ultraviolet radiation and undesirable degradation during working, such as extrusion. Some stabilising agents, such as epoxidised soya bean oils, also act as secondary plasticisers. Lubricants which can be used are, for example, stearates, stearic acid and polyethylene of low molecular weight. These constituents can be used in a concentration of up to 20% by weight of the total composition.

Fillers and additives which the polymeric carrier materials contain, if appropriate, are to be understood as meaning substances which are known per se, such as, for example, fillers and short fibres on an inorganic or organic basis, colouring agents, such as dyestuffs and coloured pigments, water-binding agents, surface-active solid substances or pH-stabilising agents.

Examples which may be mentioned of inorganic fillers are baryte, titanium dioxide, quartz sand, kaolin, carbon black and glass microbeads. Of the organic fillers, for example, powders based on polystyrene or polyvinyl chloride can be employed.

Possible short fibres are, for example, glass fibres of 0.1 to 1 mm length or fibres of an organic origin, such as, for example, polyester fibres or polyamide fibres. In order to impart the desired coloration to the polymeric carrier materials, the dyestuffs or coloured pigments on an organic or inorganic basis which are known per se for colouring polymers can be used, such as, for example, iron oxide pigments or chromium oxide pigments or phthalocyanine- or monoazo-based pigments. The preferred water-binding agents are zeolites. Solid surface-active substances which may be mentioned are, for example, cellulose powder, active charcoal, silicic acid preparations and chrysotile asbestos.

For production of the shaped articles according to the invention, the various constituents can be mixed in the dry state by known mixing processes, and moulded by known extrusion or injection moulding processes.

It is furthermore possible to mix the individual components by dissolving them in a common solvent, and then precipitating the mixture in a suitable non-solvent. In this procedure, the solution is preferably forced through a die into a precipitating bath and the coagulating material formed is drawn off as filaments (wet spinning process). The precipitation is preferably carried out by means of the known dry and wet spinning processes.

The choice of processing process for production of the shaped articles according to the invention in principle depends in industry on the Theological properties of the shaped article material and the shape of the desired structure. The processing processes can be adjusted according to the processing technology or according to the type of shaping. In the case of processing technology, the processes can be classified according to the Theological states passed through during them. Pouring, pressing, spraying and spreading accordingly are suitable for viscous shaped article materials, and injection moulding, extrusion, calendering, milling and if appropriate kneading are suitable for elastoviscous polymers.

Classified according to the type of shaping, the shaped articles according to the invention can be produced by casting, dipping, compression moulding, injection moulding, extrusion calendering, embossing, bending, deep-drawing, spinning and the like.

These processing processes are known and do not require more detailed explanation.

EXAMPLE 1

To produce shaped articles according to the invention containing active compound, a) a mixture of 30.6 parts by weight of imidacloprid, 0.2 part by weight of triadimenol and 0.2 part by weight of precipitated silicic acid and b) 69 parts by weight of the polymeric carrier material copoly (hydroxybutyric acid/hydroxyvaleric acid) (Biopol) were metered separately into a twin screw extruder via differential balances.

The components were homogenised in the extruder at 160° C. in the course of 4 minutes, and the melt was extruded into a water bath at a throughput of 1 kg/h.

After granulation and drying, the moulding composition containing active compound was shaped to rods, pins, strips and sheets with the aid of an injection moulding machine at 150° C.

EXAMPLE 2

Mixture a) from Example 1 was extruded at 190° C., in the manner described in that example, with b) 69 parts by weight of the polymeric carrier material poly(11-aminoundecanoic acid), and the mixture was then injection moulded to shaped articles.

EXAMPLE 3

In the manner described in Example 1, a) a mixture of 20 parts by weight of cyfluthrin, 0.1 part by weight of triadimenol, 80 parts by weight of β-cyclodextrin and 50 parts by weight of Carbowax 20 M and b) 150 parts by weight of the polymeric carrier material copoly (hydroxybutyric acid/hydroxyvaleric acid) (Biopol) were extruded at 160° C. and injection moulded to shaped articles.

EXAMPLE 4

In the manner described in Example 1, a) a mixture of 200 parts by weight of triadimenol and 2 parts by weight of precipitated silicic acid and b) 198 parts by weight of the polymeric carrier material copoly(hydroxybutyric acid/hydroxyvaleric acid) (Biopol) were extruded at 160° C. and injection moulded to shaped articles.

EXAMPLE 5

A mixture of 105 parts by weight of carbofuran, 0.2 part by weight of triadimenol and 2 parts by weight of precipitated silicic acid were extruded with 150 parts by weight of the polymeric carrier material poly(ε-caprolactone) at 145° C. in the manner described in Example 1.

The melt strand was drawn off at a rate of 35 m/minute, so that a cable having a diameter of about 1 mm was formed, and, after cooling in a water bath, was wound onto a bobbin.

Pins 2 cm long were produced by subsequent cutting of the cable.

EXAMPLE 6

By the procedure described in Example 5, a mixture of 105 parts by weight of fenamiphos, 2 parts by weight of triadimenol and 2 parts by weight of precipitated silicic acid was processed with 295 parts by weight of poly(ε-caprolactone) at 145° C. to give a shaped strand.

EXAMPLE 7

By the procedure described in Example 5, a mixture of 10.8 parts by weight of mefenacet, 0.2 part by weight of triadimenol and 2 parts by weight of precipitated silicic acid was processed with 87 parts by weight of a polyamide 6, 36 (Priadit 2022) at 155° C. to give a shaped strand.

EXAMPLE 8

A mixture of 30 parts by weight of triadimenol and 0.2 part by weight of precipitated silicic acid was extruded with 69.8 parts by weight of a thermoplastic polyurethane having a Shore A hardness of 88, prepared from a poly(1,4-butanediol adipate)-diol of average molecular weight 2250 and an OH number of 50, 4,4'-diisocyanatodiphenylmethane and 1,4-butanediol (Desmopan 385), at 200° C. in the manner described in Example 1 and granulated.

The dried granules containing active compound were melted in an extrusion spinning apparatus and spun to a 5-filament thread, while cooling with water.

| Spinning conditions: | Extruder temperature: | 193° C. |
|---|---|---|
| | Die temperature: | 192° C. |
| | Die (hole number/diameter: | 5/1.0 mm |
| | Screen filter: | 10 000 mesh/cm$^2$ |
| | Take-off: | 60 m/min |
| | Throughput: | 13.8 g/min |

A multifilament containing active compound and having an overall titre of 300 dtex (180 μm diameter) was obtained.

EXAMPLE 9

A mixture of 20 parts by weight of cyfluthrin, 0.1 part by weight of triadimenol, 80 parts by weight of β-cyclodextrin and 50 parts by weight of Carbowax 20 M was melted and mixed in an extruder with 150 parts by weight of a poly (ether-ester) elastomer (Hytrel G-3548) at 185° C. in the manner described in Example 1.

The melt was forced at 190° C. through a 75 mm wide slit die with a gap height of 0.5 mm, cooled by blowing on air and taken off at a rate of 5 m/minute by means of a Teflon conveyor belt. Films having a thickness of about 50 μm were obtained in this manner.

EXAMPLE 10

29.7 g (49.5 parts by weight) of poly(ε-caprolactone) were melted in a kneader of the Haake Rhoemix type at 150° C. and 50 revolutions per minute, and a mixture of 20 g (33.3 parts by weight) of tolylfluanid, 5 g (8.3 parts by weight) of tebuconazole, 0.3 g (0.5 part by weight) of precipitated silicic acid and 5 g (8.3 parts by weight) of dextrin was added. For homogenisation, the mixture was kneaded for a further 5 minutes after the active compound formulation had been added.

The resulting composition containing active compound was shaped in a press under a pressure of 200 bar and at 150° C. to give sheets of 100 cm² surface area and 2 mm thickness.

EXAMPLE 11

A mixture of 70 parts by weight of imidacloprid, 29 parts by weight of polyethyleneglycol(MW 7800 to 9000) and 1 part of hydrophobic synthetic silica(Sipernat D 17 from Degussa) was pulverized. The components were mixed in a blender until they became homogeneous. 1.44 g of the homogeneous powder was transferred into a cylinder of 6 mm in diameter of a tabletting machine and the contents were compressed with a piston up to 600 kg in total. The height of the obtained pellet was 40 mm.

EXAMPLE 12

A mixture of 70 parts by weight of imidacloprid, 27 parts by weight of carnauba wax and 3 parts by weight of hydrous synthetic silica was treated in the way in Example 11 to have homogeneous powder. 1.44 g of the homogeneous powder was transferred into a cylinder of 9 mm in diameter of a tabletting machine and the contents were compressed with a piston up to 600 kg in total, The height of the obtained pellet was 18 mm.

EXAMPLE 13

A mixture of 25 parts by weight of imidacloprid, 31 parts by weight of ethyleneglycol(MW 3000 to 7000) and 3 parts by weight of hydrous synthetic silica was placed in a stainless steel container and the contents were melted by heating. The molten mixture was agitated to be homogeneous. 1.44 g of the homogeneous molten mixture was transferred into a metal mould of 9 mm in diameter. After cooling, a pellet of 9 mm in diameter and of 18 mm in height was obtained.

EXAMPLE 14

A mixture of 2 parts by weight of imidacloprid, 38 parts by weight of bentonite and 60 parts by weight of clay was mixed in a blender to have a homogeneous mixture. The mixture was kneaded by adding 18 parts of water. The kneaded material was dried with a fluidized bed dryer. The length of the dried pellet were cut into 1 mm in length.

EXAMPLE 15

Test on Cotton Aphid (*Aphis gosyppi*)

| Preparation of the shaped compositions | |
|---|---|
| imidacloprid | 2.0 parts by weight |
| Bentonite | 38.0 parts by weight |
| Clay | 60.0 parts by weight |

The above-mentioned components are intimately mixed and then formulated into granulated shaped compositions according to the conventional granulation process.

Method

Cucumber plants (cv, Sharp) each grown to a height of about 180 cm were allowed to naturally inhabit cotton aphids having resistances to organic phosphorus compositions and carbamate compositions.

To each of the test plants was embedded a predetermined dosage of the shaped composition prepared above under such conditions that the adult insects inhabited the plant at a rate of 70 pieces a leaf, they were allowed to stand at 28° C. in a hothouse, and then the number of the living insects were determined on seven, fourteen, twenty-one and twenty-eight days respectively after the treatment, thus calculating the control effect in % according to the following equation: The results of the test is shown in Table 1.

$$\text{Control effect (\%)} = \left\{ 1 - \frac{\left(\begin{array}{c}\text{the number of living}\\ \text{insects counted in a test} \times\\ \text{section after treatment}\end{array}\right)}{\left(\begin{array}{c}\text{the initial number}\\ \text{of living insects in}\\ \text{a untreated section}\end{array}\right)} \right\} \times 100$$

$$\frac{\text{the number of living}}{\text{insects counted in the test} \times}$$
section before treatment the number of living insects in the untreated section when the counting has been carried out in the treated test section

TABLE 1

| Concentration of the active component | Control Effect (%) | | | |
|---|---|---|---|---|
| mg/plant body | 7 days | 14 days | 21 days | 28 days |
| 3.0 | 100 | 100 | 100 | 95 |
| 2.5 | 100 | 100 | 98 | 93 |
| 2.0 | 98 | 100 | 95 | 90 |
| 1.5 | 93 | 96 | 90 | 85 |

The number of living insects per leaf in the non-treated section counted in correspondence to the above-mentioned respective count days in the test section.

|  | Before treatment | 7 days | 14 days | 21 days | 28 days |
| --- | --- | --- | --- | --- | --- |
| Number of insects | 65 | 173 | 566 | 845 | 840 |

EXAMPLE 16

For the simultaneous control against aphids, thrips and whiteflies on vegetables.

A cucumber plant being 2 months after transplanting on the ground in the greenhouse was treated on its stem by insert with a small solid bar (1 mm in diameter, 5 mm in length, 70% of imidacloprid, 30% PEG). 5 plants per plot were used the test.

7 and 21 days after the treatment, living insects on the plants were investigated, and then the mortality was calculated comparing with control plots.

|  | Mortality (%) | | | | | |
| --- | --- | --- | --- | --- | --- | --- |
|  | A | | B | | C | |
|  | 7 | 21 | 7 | 21 | 7 | 21 days |
| Test sample plots | 100 | 100 | 100 | 100 | 100 | 100 |
| Control plots | 0 | 0 | 0 | 0 | 0 | 0 |

A: Cotton aphid (*Aphis gossypii*)
B: Greenhouse whitefly (*Trialeurodes vaporariorum*)
C: Thrips palmi (Southern yellow thrips)

EXAMPLE 17

For the control of Japanese pine sawyer (*Monochamus alternatus*) on Japanese pine tree.

Solid shaped plant treatment material (6 mm in diameter, 40 mm in length, 70% imidacloprid, 30% PEG) was inserted into a hole of the trunk of J. pine tree at 3 bars per 1 tree (Ca. 10–15 cm of trunk in diameter) in early spring. 5 trees per plot were used the test.

10 heads of newly emerged adults of. J. pine sawyer were infested artificially on a top wig of the tree at the end of July. Mortality was investigated 3 days after infestation.

|  | Mortality (%) |
| --- | --- |
| Test sample plot | 100 |
| Control plot NIT 280 | 0 |

EXAMPLE 18

For the control of Pine wood nematode (*Bursaphelenchus xylophilus*) on Japanese pine tree.

Solid shaped plant treatment material (6 mm in diameter, 40 mm in length, 60% mesulfenfos, 40% PEG) was inserted into a hole of the trunk of J. pine tree at 5 bars per 1 tree (Ca. 10–15 cm of the trunk in diameter) in early spring. 5 trees per plot were used the test.

3000 heads of the P.W. nematoda were infested artificially on a top wig of the tree at the and of July.

The death of the trees was investigated 3 months after infestation.

|  | % of the death of the trees |
| --- | --- |
| Test sample plot | 0 |
| Control plot | 100 |

It will be appreciated that the instant specification and claims are set forth by way of illustration and not limitation, and that various modifications and changes may be made without departing from the spirit and scope of the present invention.

We claim:

1. A process for making rods and pins to be pressed or knocked into sap conduction paths of individual plants comprising organic insecticides and/or fungicides contained in a polymeric carrier material as a matrix, wherein said carrier material is selected from the group consisting of poly-ε-caprolactone and polyhydroxyalkanoates, said process comprising homogenizing 30.6 parts by weight of imidacloprid, 0.2 parts by weight of triadimenol, 0.2 parts by weight of precipitated silicic acid and 69 parts by weight of copoly(hydroxybutyric acid/hydroxyvaleric acid) at 160° in the course of 4 minutes, extruding the result into a water bath, and granulating, drying and shaping at 150° C.

2. The agent according to claim 1 wherein said insecticide is selected from the group consisting of carbamates, pyrethroids, benzoylureas, triazines, nitromethylenes, nitroguanidines, cyanamides, juvenile hormones and juvenoid synthetic compounds.

3. The agent according to claim 1 wherein said fungicides are selected from the group consisting of sulfenamides, benzimidazoles, thiocyanates, quaternary ammonium compounds, phenols, azoles, iodopropargyl derivatives, isothiazolines, benzisothiazolinones, cyclopentene-isothiazolines, nitrites, benzothiazoles and quinolines.

4. The agent according to claim 2 wherein said insecticide is selected from the group consisting of azinphosethyl, azinphos-methyl, I-(4-chlorophenyl)-4-(O-ethyl-S-propyl)-phosphoryloxypyrazole (TIA-230), chlorpyrifos, coumaphos, demeton, demeton-S-methyl, diazinon, dichlorvos, dimethoate, ethoprophos, etrimfos, fenitrothion, fention, heptenophos, parathion, parathion-methyl, phosalone, phoxion, pirimiphosethyl, pirimiphos-methyl, profenofos, prothiofos, sulprofos, triazophos, trichlorphon, aldicarb, bendiocarb, BPMC (2-(1-methylpropyl)-phenyl methylcarbamate), butocarboxime, butoxycarboxime, carbaryl, carbofuran, carbosulphan, cloethocarb, isoprocarb, methomyl, oxamyl, pirimicarb, promecarb, propoxur, thiodicarb, allethrin, alphamethrin, bioresmethrin, byfenthrin (FMC 54800), cycloprothrin, cyfluthrin, decamethrion, cyhalothrin, cypermethrin, deltamethrin, alpha-cyano-3-phenyl-2-methylbenzyl 2,2,-dimethyl-3-(2)-chloro-2-trifluoromethylvinyl)cyclopropanecarboxylate, fenpropathrin, fenfluthrin, fenvalerate, flucythrinate, flumethrin, fluvalinate, permethrin resmethrin, and 1-[(6-chloro-3-pyridinyl)-methyl]-4,5-dihydro-N-nitro-1H-imidazol-2-amine.

5. The agent according to claim 1 wherein said insecticides is selected from the group consisting of nitromethylenes, nitroguanidines and cyanimides of the formula I

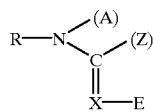 (I)

in which

R represents hydrogen or optionally substituted acyl, alkyl, aryl, aralkyl, heteroaryl or heteroarylalkyl radicals;

A represents a monofunctional group from the series comprising hydrogen, acyl, alkyl and aryl, or represents a bifunctional group, which is linked to the radical Z;

E represents $NO_2$ or CN;

X represents the radicals —CH= or =N—, wherein the radical —CH= can be linked to the radical Z instead of an H atom; and Z represents a monofunctional group from the series comprising alkyl, —O—R or

or represents a bifunctional group, which is linked to the radical A or the radical X.

6. The agent according to claim 1 in which the insecticide is selected from the group consisting of formulae II and III:

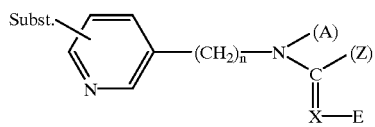 (II)

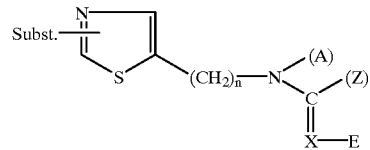 (III)

in which

Subst. represents halogen, n represents 1 or 2,

A represents a monofunctional group from the series comprising hydrogen, acyl, alkyl and aryl, or represents a bifunctional group, which is linked to the radical Z;

E represents $NO_2$ or CN;

X represents the radicals —CH= or =N—, wherein the radical —CH= can be linked to the radical Z instead of an H atom; and Z represents a monofunctional group from the series comprising alkyl, —O—R, —S—R or

or represents a bifunctional group, which is linked to the radical A or the radical X, R represents hydrogen or optionally substituted acyl, alkyl, aryl, aralkyl, heteroaryl or heteroarylalkyl radicals.

* * * * *